| United States Patent [19] | [11] Patent Number: 4,792,558 |
| Sunkara et al. | [45] Date of Patent: Dec. 20, 1988 |

[54] CASTANOSPERMINE FOR INHIBITING TUMOR METASTASIS

[75] Inventors: Sai P. Sunkara; Barry L. Rhinehart; Paul S. Liu, all of Cincinnati, Ohio

[73] Assignee: Merrell Dow Pharmaceuticals Inc., Cincinnati, Ohio

[21] Appl. No.: 55,589

[22] Filed: May 29, 1987

[51] Int. Cl.$^4$ ............................................. A61K 31/44
[52] U.S. Cl. ..................................................... 514/299
[58] Field of Search ........................................ 514/299

[56] References Cited

PUBLICATIONS

Chemical Abstracts, 105:202820q (1986).
Martin J. Humphries, et al., *Cancer Research*, 46, 5215–5222 (1986).
Tohru Kino, et al., *The Journal of Antibiotics*, 38, 936–940 (1985).

*Primary Examiner*—Jerome D. Goldberg
*Attorney, Agent, or Firm*—John J. Kolano

[57] ABSTRACT

A method for the inhibition of tumor metastases is described herein. The method makes use of the administration of castanospermine.

8 Claims, 1 Drawing Sheet

CASTANOSPERMINE FOR INHIBITING TUMOR METASTASIS

BACKGROUND OF THE INVENTION

The spread of cancer cells from a primary tumor site to distant organs is known as metastasis. Metastasis has been considered one of the most intriguing aspects of the pathogenesis of cancer. This is certainly true to the extent that cancer tumor metastasis is responsible for most therapeutic failures when the disease is treated, as patients succumb to the multiple tumor growth. The extent to which metastasis occurs varies with the individual type of tumor. Melanoma, breast cancer, lung cancer and prostate cancer are particularly prone to metastasize.

When metastasis takes place, the secondary tumors can form at a variety of sites in the body, with one of the more common sites for metastasis being the lung.

Thus, inhibition of tumor metastasis to any extent would be beneficial and this would be true regardless of whether the agent involved in the inhibition had any effect on the primary tumor. Of course, if the agent also inhibited the primary tumor, this would be an additional advantage for the agent.

SUMMARY OF THE INVENTION

It has now been found that castanospermine or its pharmaceutically acceptable salts are useful in the inhibition of tumor metastasis. Castanospermine is an indolizidine alkaloid which is known systematically as (1S,6S,7R,8R,8aR)-1,6,7,8-tetrahydroxyindolizidine. Pharmaceutically acceptable salts of castanospermine can be exemplified by those with inorganic acids such as hydrochloric acid, hydrobromic acid, sulfuric acid and phosphoric acid; and with organic acids such as acetic acid, methanesulfonic acid and p-toluenesulfonic acid.

More specifically, the present invention relates to a method for inhibiting the formation of tumor metastases comprising the administration of an amount, which is safe and sufficient to inhibit the formation of tumor metastases, of castanospermine or a pharmaceutically acceptable salt thereof to a patient having melanoma, breast cancer, lung cancer or prostate cancer.

The experiments below demonstrate the ability of castanospermine or its compositions to inhibit metastasis of tumor cells and, particularly, metastasis of tumor cells to lungs. The lungs provide a convenient organ for the study of metastasis in the animal body. The effect of castanospermine on certain tumor cells is also demonstrated below.

Lewis lung carcinoma (3LL) cells ($1 \times 10^5$/animal) were injected subcutaneously at the interscapular region of C57/BL mice on Day 0. Castanospermine was injected i.p. once a day at the doses and the schedule indicated below. Groups of 6 mice were used for each dose schedule. At the end of Day 18, animals were sacrificed, and the tumors dissected and weighed. The lungs were fixed and the number of metastatic foci were quantitated. The results in Table 1 show that castanospermine inhibited tumor growth while the results in Table 2 show that castanospermine inhibited metastasis in the lungs.

TABLE 1

EFFECT OF CASTANOSPERMINE ON THE GROWTH OF LEWIS LUNG CARCINOMA (3LL) IN MICE

| Treatment | Schedule | Tumor weight (gr) (Mean ± SE) | % Inhibition |
|---|---|---|---|
| Control | | 7.3 ± 0.7 | |
| Castanospermine | | | |
| 100 mg/kg | Day 1-15 | 6.0 ± 0.4 | 18 |
| 100 mg/kg | Day 7-17 | 5.9 ± 1.4 | 20 |
| 250 mg/kg | Day 1-15 | 5.2 ± 0.8 | 29 |
| 250 mg/kg | Day 7-17 | 5.7 ± 0.1 | 23 |
| 500 mg/kg | Day 1-15 | 5.5 ± 0.5 | 25 |
| 500 mg/kg | Day 7-17 | 4.4 ± 0.3 | 40 |

TABLE 2

EFFECT OF CASTANOSPERMINE ON THE METASTASIS OF LEWIS LUNG CARCINOMA (3LL) IN MICE

| Treatment | Schedule | Metastatic Foci (Mean ± SE) | % Inhibition |
|---|---|---|---|
| Control | | 57.7 ± 11.4 | |
| Castanospermine | | | |
| 100 mg/kg | Day 1-15 | 32.1 ± 5 | 32 |
| 100 mg/kg | Day 7-17 | 26.5 ± 3 | 54 |
| 250 mg/kg | Day 1-15 | 54.7 ± 7 | 6 |
| 250 mg/kg | Day 7-17 | 46.3 ± 17 | 20 |
| 500 mg/kg | Day 1-15 | 29.7 ± 5 | 49 |
| 500 mg/kg | Day 7-17 | 26.7 ± 3 | 54 |

In another experiment, $1 \times 10^5$ viable B16 melanoma F10 line cells were injected i.v. through the tail vein of C57/BL mice. Castanospermine was then administered i.p. daily as indicated below. At the end of 15 days, the animals were sacrificed and the number of metastatic foci in the lungs were quantitated. The results observed are summarized in Table 3 below with n indicating the number of animals used in the test.

TABLE 3

EFFECT OF CASTANOSPERMINE ON THE EXPERIMENTAL METASTASIS OF B16 MELANOMA (F10)

| Treatment | Schedule | Metastatic Foci (Mean + SE) | % Inhibition |
|---|---|---|---|
| Control | | 75.8 ± 5.4 (n = 10) | — |
| Castanospermine | | | |
| 50 mg/kg | Day 1-14 | 41.0 ± 2.9 (n = 5) | 45 |
| 100 mg/kg | Day 1-14 | 25.5 ± 2.4 (n = 10) | 67 |
| 100 mg/kg | Day 7-14 | 39.4 ± 4.6 (n = 5) | 48 |
| 250 mg/kg | Day 1-14 | 19.3 ± 1.3 (n = 5) | 75 |
| 250 mg/kg | Day 7-14 | 31.5 ± 8.1 (n = 5) | 58 |

It should be evident from the results in the above table that castanospermine significantly inhibited metastasis in the animals when the treatment was started either on day 1 or day 7 after tumor inoculation.

The method of treatment by inhibition of metastasis disclosed and claimed herein may be used alone or in combination as part of a treatment regimen for an animal or human patient having a cancer that is prone to metastasis, particularly, melanoma, breast cancer, lung cancer and prostate cancer. The treatment to inhibit the formation of metastases is best administered as soon after the detection of the cancer as possible. By utilizing the treatment regimen in patients at an early stage, the treating physician maximizes the chances that significant metastasis has not yet occurred. This maximizes chances for successful treatment. In such a regimen, the castanospermine or its salts may, and generally will, be administered in combination with another form of therapy which controls the primary tumor itself. The other therapy in such a combination can include, but is not limited to, radiation therapy or the administration of compatible antitumor or antineoplastic agents. Examples of such antineoplastic agents include melphalan, lomustine capsules, cyclophosphamide, fluorouracil and also ornithine decarboxylase inhibitors such as difluoromethylornithine (DFMO), 6-heptyne-2,5-diamine and (E)-2,5-diamino-2-(fluoromethyl)-3-pentenoic acid methyl ester dihydrochloride. The treatment described in the present application may also be used conjointly with (i.e., either preceding or subsequent to) a surgical procedure to remove the primary tumorous material from the body. Frequently, surgical procedures to remove tumorous material from the body are avoided because of the fear that metastasis of tumor cells will occur as a result of the physical manipulation involved. However, if castanospermine or its salts are administered to the patient prior to the surgical procedure, then the risk of metastasis which may result from surgery can be reduced and surgery would be a more attractive treatment option.

Within the scope of sound medical judgment, the dosage of castanospermine or its salts and the method of administration used in the present invention will vary with the severity and nature of the particular condition being treated, the duration of treatment, the adjunct therapy used, the age and physical condition of the patient, and like factors within the specific knowledge and expertise of the attending physician. However, single dosages can typically range from 0.01 to 2000 milligrams per kilogram of body weight, preferably 1 to 200 milligrams per kilogram (unless otherwise specified, the unit designated "mg/kg", as used herein, refers to milligrams per kilogram of body weight). Up to four doses per day can be used routinely, but this can be varied according to the needs of the patient, consistent with a sound benefit/risk ratio. Variation in patient response may be expected but the higher dosages within the ranges indicated are usually required in the case of oral administration while the lower dosages indicated would apply for intravenous administration.

For purposes of oral administration, the castanospermine or its salts can be formulated in the form of capsules, tablets or granules while for intravenous administration, the active material can be formulated in an appropriate solution. In any case, the active compound is mixed with an appropriate pharmaceutical carrier.

As used herein, the term "pharmaceutical carrier" denotes a solid or liquid filler, diluent or encapsulating substance. Some examples of the substances which can serve as pharmaceutical carriers are sugars, such as lactose, glucose and sucrose; starches, such as corn starch and potato starch; cellulose and its derivatives, such as sodium carboxymethyl cellulose, ethyl cellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols, such as propylene glycol, glycerin, sorbitol, mannitol, and polyethylene glycol; agar; alginic acid; pyrogen-free water; isotonic saline; and phosphate buffer solutions, as well as nontoxic compatible substances used in pharmaceutical formulations. Wetting agents and lubricants, such as sodium lauryl sulfate, as well as coloring agents, flavoring agents, tableting agents, and preservatives, can also be present. Tableting or any other formulation is done using conventional techniques. Additional information about suitable pharmaceutical carriers and formulation techniques are found in standard texts, such as Remington's *Pharmaceutical Sciences*, Mack Publishing Company, Easton, Pa.

The pharmaceutical carrier employed in conjunction with the castanospermine or its salts is used at a concentration sufficient to provide a practical size to dosage relationship. Preferably, the pharmaceutical carrier comprises from about 0.1% to 99% by weight of the total composition.

What is claimed is:

1. A method for inhibiting the formation of tumor metastases comprising administering an amount, which is safe and sufficient to inhibit the formation of tumor metastases, of castanospermine or a pharmaceutically acceptable salt thereof to a patient having melanoma, breast cancer, lung cancer or prostate cancer.

2. A method according to claim 1 wherein the patient has melanoma or lung cancer.

3. A method according to claim 1 wherein the patient has melanoma.

4. A method according to claim 1 wherein the patient has lung cancer.

5. A method according to claim 1 wherein the daily dosage of compound administered is from about 0.01 to about 2,000 mg/kg body weight.

6. A method according to claim 5 wherein the daily dosage administered is from 1 to about 200 mg/kg body weight.

7. A method according to claim 5 carried out in preparation for a surgical procedure to remove tumorous material.

8. A method according to claim 5 wherein the compound is administered promptly after the detection of the cancer.

* * * * *